(12) United States Patent
Kassab et al.

(10) Patent No.: US 8,231,646 B2
(45) Date of Patent: Jul. 31, 2012

(54) DEVICE AND METHODS FOR CONTROLLING BLOOD PERFUSION PRESSURE USING A RETROGRADE CANNULA

(75) Inventors: Ghassan S. Kassab, Zionsville, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 801 days.

(21) Appl. No.: 11/997,139

(22) PCT Filed: Jul. 28, 2006

(86) PCT No.: PCT/US2006/029223
§ 371 (c)(1),
(2), (4) Date: May 14, 2008

(87) PCT Pub. No.: WO2007/016260
PCT Pub. Date: Feb. 8, 2007

(65) Prior Publication Data
US 2008/0234658 A1    Sep. 25, 2008

Related U.S. Application Data

(60) Provisional application No. 60/703,422, filed on Jul. 29, 2005.

(51) Int. Cl.
*A61M 29/00* (2006.01)
(52) U.S. Cl. ........ 606/194; 606/154; 606/191; 606/200; 604/48; 604/501; 604/503; 604/505
(58) Field of Classification Search ............ 604/48, 604/96.01, 501, 503, 505, 507; 606/154, 606/200
See application file for complete search history.

(56) References Cited

U.S. PATENT DOCUMENTS

| | | | |
|---|---|---|---|
| 4,459,977 A | 7/1984 | Pizon et al. | |
| 4,850,969 A | 7/1989 | Jackson | |
| 4,917,667 A | 4/1990 | Jackson | |
| 4,927,412 A | 5/1990 | Menasche | |
| 5,533,957 A | 7/1996 | Aldea | |
| 5,655,548 A | 8/1997 | Nelson et al. | |
| 5,833,662 A | 11/1998 | Stevens | |
| 5,908,407 A | 6/1999 | Frazee et al. | |
| 6,045,531 A * | 4/2000 | Davis | 604/101.05 |
| 6,186,972 B1 | 2/2001 | Nelson et al. | |
| 6,228,111 B1 | 5/2001 | Tormala et al. | |
| 6,368,346 B1 | 4/2002 | Jadhav | |
| 6,447,539 B1 | 9/2002 | Nelson et al. | |
| 6,500,145 B1 | 12/2002 | Bicakci et al. | |
| 6,613,037 B2 | 9/2003 | Khosravi et al. | |
| 6,926,689 B2 | 8/2005 | Scheule | |

(Continued)

OTHER PUBLICATIONS

International Searching Authority, International Search Report, Mar. 1, 2007.

(Continued)

*Primary Examiner* — Gary Jackson
*Assistant Examiner* — Kevin Everage
(74) *Attorney, Agent, or Firm* — Ice Miller LLP

(57) ABSTRACT

Devices and methods are disclosed for the control of blood perfusion pressure within a blood vessel that undergoes arterialization. A cannula is introduced that contains a stenosis that either resorbs or is removed in time, allowing a gradual increase in blood pressure between two blood passages connected at either ends of the cannula. Particular emphasis has been made with the use of the cannula for the vessels in the heart.

24 Claims, 6 Drawing Sheets

U.S. PATENT DOCUMENTS

| | | |
|---|---|---|
| 7,004,925 B2 | 2/2006 | Navia et al. |
| 7,004,926 B2 | 2/2006 | Navia et al. |
| 7,473,237 B2 | 1/2009 | Navia et al. |
| 7,819,856 B2 | 10/2010 | Bates |
| 2002/0077581 A1 | 6/2002 | Davidner et al. |
| 2003/0125798 A1 | 7/2003 | Martin |
| 2003/0130668 A1* | 7/2003 | Nieman et al. ............. 606/108 |
| 2003/0181843 A1 | 9/2003 | Bibber et al. |
| 2004/0172004 A1 | 9/2004 | Mohl |
| 2004/0267084 A1 | 12/2004 | Navia et al. |
| 2005/0101902 A1 | 5/2005 | Navia et al. |
| 2006/0074399 A1* | 4/2006 | Bates ............................. 604/522 |
| 2006/0085028 A1* | 4/2006 | Boock ........................... 606/200 |
| 2006/0184088 A1 | 8/2006 | Van Bibber et al. |
| 2006/0195060 A1 | 8/2006 | Navia et al. |
| 2007/0010781 A1 | 1/2007 | Vijay |

OTHER PUBLICATIONS

International Searching Authority, Written Opinion of the International Searching Authority, Mar. 1, 2007.

* cited by examiner

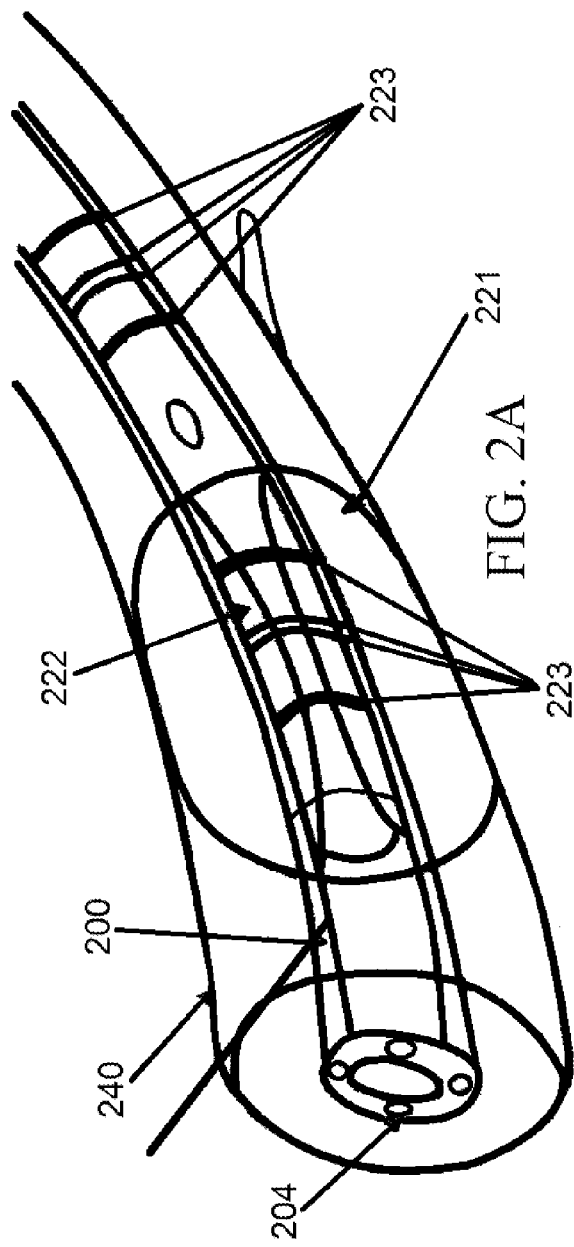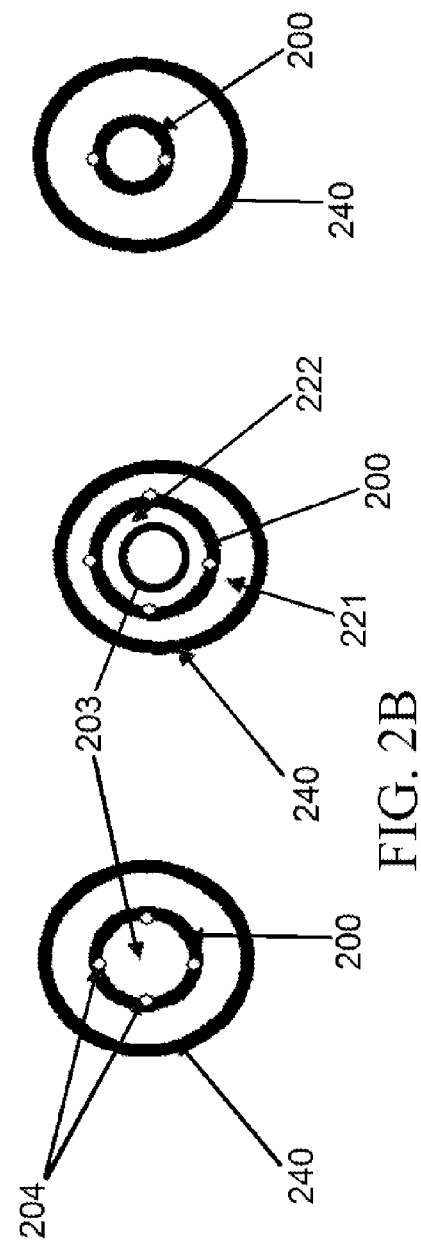
FIG. 2A
FIG. 2B

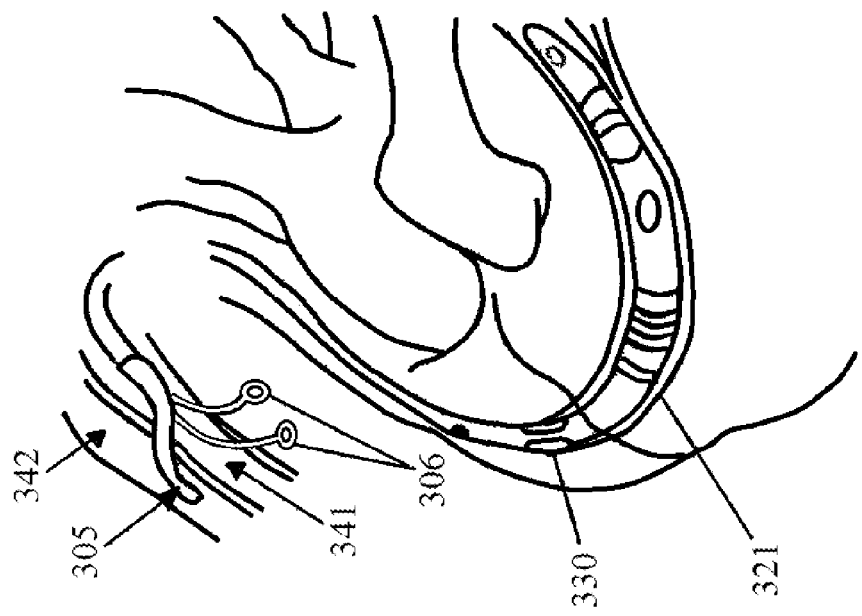
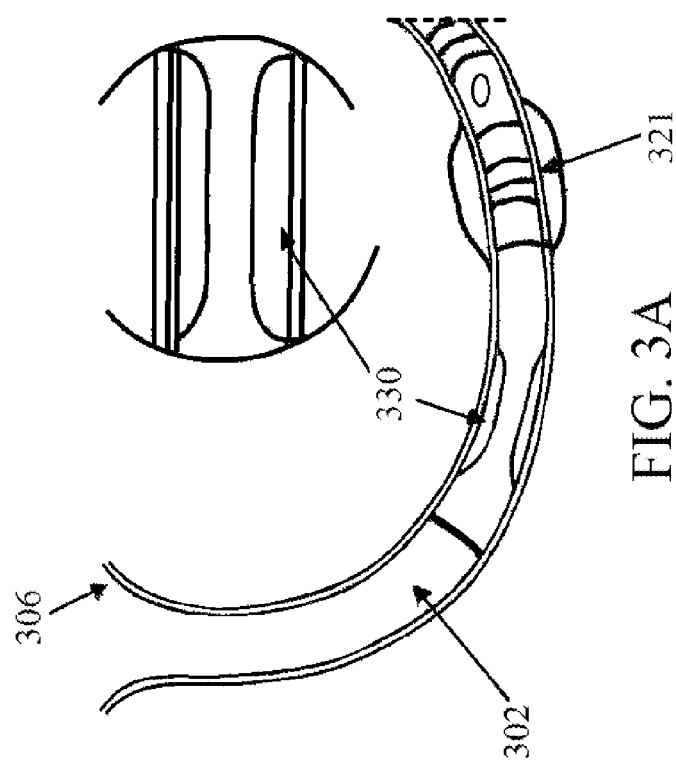
FIG. 3B
FIG. 3A

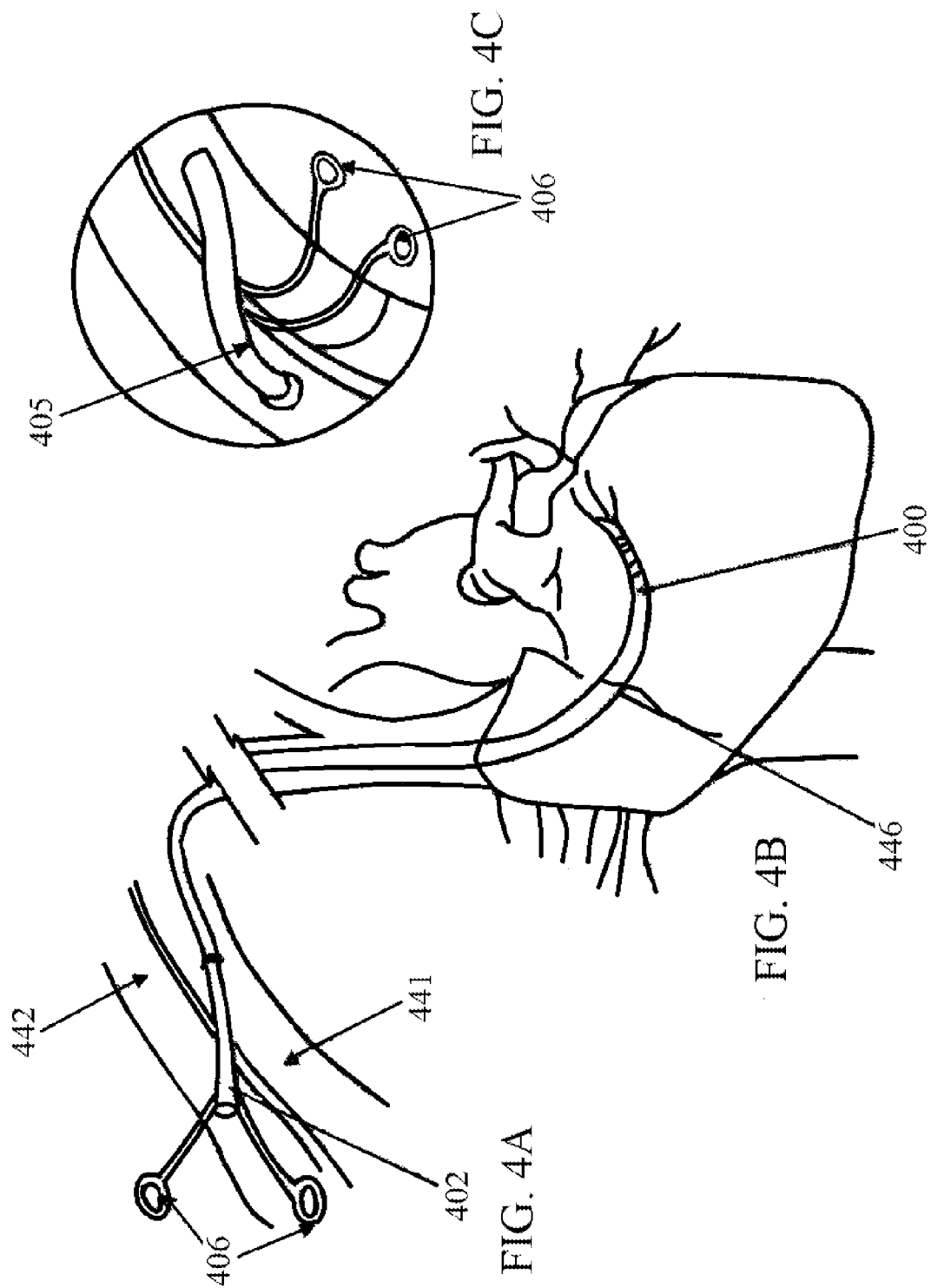

DEVICE AND METHODS FOR CONTROLLING BLOOD PERFUSION PRESSURE USING A RETROGRADE CANNULA

RELATED APPLICATIONS

The present application is a U.S. National Stage Application of the International Patent Application Serial No, PCT/US2006/029223, filed Jul. 28, 2006, which claims priority to U.S. Provisional Patent Application Ser. No. 60/703,422, filed Jul. 29, 2005. The contents of each of these applications are hereby incorporated by reference in their entirety into this disclosure.

BACKGROUND OF THE INVENTION

1. Field of the Invention

The present invention relates generally to controlling blood pressure. More particularly, the present invention relates to devices and methods for controlling blood pressure using a retrograde cannula.

2. Background of the Invention

The concept of myocardial salvage through coronary sinus intervention dates back to the nineteenth century. The objective has been to increase the flow of oxygenated blood to the ischemic myocardium by perfusing the coronary bed retrogradely from the coronary sinus; i.e., coronary retroperfusion. To date, a number of retroperfusion methods have been developed. Pressure-controlled intermittent coronary sinus occlusion (PICSO) has been used in conjunction with a balloon-tipped catheter positioned just beyond the orifice of the coronary sinus with the proximal end connected to a pneumatic pump that automatically inflates and deflates the balloon according to a preset cycle. Synchronized retrograde perfusion (SRP) and simplified retroperfusion are other techniques that actively pump arterial and venous blood in the former and the latter, respectively. The left ventricle-powered coronary sinus retroperfusion technique has focused on driving left ventricular blood into the coronary sinus through a surgically created left ventricle to coronary sinus shunt.

Prior studies have shown the efficacy of venous retroperfusion. It has been demonstrated that (1) coronary venous bypass-graft (CVBG) or percutaneous in situ coronary venous arterialization (PICVA) permits survival in the presence of LAD arterial ligation as compared with the uniform non-viability of just LAD arterial ligation without retroperfusion; (2) retroperfusion is effective because it perfuses all layers of the heart, including the subendocardium; and (3) considerable recovery of regional myocardial function with low regional capillary blood flows and low levels of retrograde arterial outflow provide evidence for possible oxygen delivery via the intramyocardial venous plexus.

The CVBG or PICVA procedure has a number of advantages over the conventional coronary artery bypass graft (CABG) procedure, because, at least in part: (1) approximately 20% of revascularization candidates have angiographically diffuse atherosclerotic changes with poor runoff or small coronary arteries which makes arterial bypass or percutaneous coronary angioplasty unlikely to succeed. In those cases, CVBG may be the procedure of choice. Furthermore, the runoff for the coronary veins are significantly larger than those of arteries and hence the surgical implementation is much easier as is the improved patency of the graft. (2) The coronary venous system of the heart rarely undergoes atherosclerotic changes. This reduces the problem of restenosis that is commonly evident with the CABG procedure and should reduce the need for multiple surgeries throughout the patient's lifespan. (3) The CVBG is surgically easier to implement than the CABG procedure and does not require cardiac arrest and the use of extracorporeal circulation. The CVBG procedure can be implemented in the beating heart with the use of a cardiac restrainer. This reduces the surgical risks and ensures quicker recovery, which is particularly important in the elderly and the severely ill patients.

To emphasize the importance of this field in terms of numbers, at the time this application was filed there were about 1.4 million annual incidences of myocardial infarction in the U.S. and an equal number in Western Europe. Approximately 20% of those patients were not good candidates for bypass because of diffuse coronary artery disease and, accordingly, had few treatment options other than heart transplant. The number of heart transplants is meager, however, about 2,000 in 2005. Many of those patients progress to heart failure and thus incur the very high cost of treatment associated therewith ($40 billion annually in the United States, representing 5.4% of total health care cost). The prospect of a device to treat such patients is great in terms of lives saved as well as costs reduction associated with heart failure.

Thus, a need exists in the art for an alternative to the conventional techniques of treating heart failure using retroperfusion such that the technique should be minimally invasive, easy to use and understand, simple to implement and effective in producing desired results.

SUMMARY OF THE INVENTION

The present invention provides devices and methods for assisting in the proper retroperfusion of various organs (e.g., brain, eye, etc.) but in particular the heart. A general goal is to develop a coronary venous retroperfusion cannula that will provide perfusion of the coronary bed retrogradely through the coronary sinus with arterial blood generated from a peripheral artery with no need for a pump. The cannula will be introduced from the axillary or femoral vein under local anesthesia and the proximal end, which consists of a graft, will be anastomosed to the axillary or femoral artery, respectively. Furthermore, the cannula will initially impose a significant pressure drop (approximately 50 mmHg) due to inflation of a balloon or an obstruction (stenosis) made of resorbable material, and hence will only transmit a fraction of the arterial pressure to the venous system. The intermediate pressure can be used to arterialize the venous system for 2 to 3 weeks and can then be raised to arterial pressure by release of the stenosis.

In the case of a resorbable material, as the material resorbs over a several week period, it will reduce the pressure drop and hence transmit more of the arterial pressure to the venous system. This addresses a major problem with coronary venous retroperfusion, which is the sudden increase in pressure (venous to arterial) that results in vessel edema and hemorrhage. Here, a novel cannula is presented which provides a gradual increase in pressure to allow the venous system to arterialize. The gradual increase in pressure allows arterializations of the venous system, which prevent vessel rupture. Some of the advantages of the present invention include, but are not limited to: (1) design of a cannula with a stenosis that will provide the desired initial pressure drop and ensure undisturbed flow into the coronary venous system; (2) pre-arterialization of the venous system to prevent edema and hemorrhage, (3) elimination of the need for a pump as blood is delivered from the patient's artery; (4) percutaneous delivery of the system with no need for open heart surgery; and (5)

delivery of cannula in the beating heart to eliminate cardiac arrest such as in bypass surgery.

Since the coronary veins do not develop arteriosclerosis, it is desirable to use these vessels as conduits for revascularization. More than 60 years ago, Roberts et al. suggested the use of coronary veins as conduits to deliver oxygenated blood in a retrograde manner in animal studies. Five years after this seminal study, Beck and colleagues performed the coronary retroperfusion procedure in humans. The method was abandoned, however, due to the high mortality rate from the edema and hemorrhage that result due to the elevated pressure. Furthermore, graft clots and atherosclerotic changes occur in the venous vessels in response to the abrupt change in pressure, which lead to progressive venous obliteration.

In order to remedy these difficulties, the present invention avoids increasing the pressure in the coronary vein from venous (10-20 mmHg) to arterial values (100-120 mmHg) in a single step. Instead, a cannula is presented that regulates the pressure in the venous system over time to a more gradual increase in pressure. This procedure allows the venous vessels to arterialize and the vessel walls to thicken in order to decrease the stress and prevent rupture of the post capillary venules. Furthermore, the gradual increase in pressure will decrease the injury response and subsequently reduce the atherosclerotic changes of the large epicardial veins.

BRIEF DESCRIPTION OF THE DRAWINGS

FIG. 2A shows a detailed version of a cannula's multi-lumen catheter with inner and outer balloons according to an exemplary embodiment of the present invention.

FIG. 2B shows cross-sectional views of exemplary embodiments of multiple lumens within a cannula according to exemplary embodiments of the present invention.

FIG. 3A shows a cannula inserted into the coronary sinus via the axillary vein according to an exemplary embodiment of the present invention.

FIG. 3B shows an embodiment of a cannula containing a resorbable stenosis according to an exemplary embodiment of the present invention.

FIG. 4A shows a minimally invasive surgical insertion of a retroperfusion cannula with direct puncture of the axillary vein and catheterization into the coronary sinus according to an exemplary embodiment of the present invention.

FIG. 4B shows the cannula of FIG. 4A after the graft is fixed in position at the coronary sinus.

FIG. 4C shows the cannula of FIG. 4A as the axillary artery is prepared and the proximal side of the graft is anastomosed to the axillary artery.

DETAILED DESCRIPTION OF THE INVENTION

The present invention describes a cannula for acute and chronic retroperfusion that is designed for percutaneous insertion into the coronary sinus and proximally connecting to the subclavian artery. This allows retroperfusion of oxygenated blood through the coronary venous system to decrease an acute ischemic area during an acute myocardial infarction event.

Figure 1:
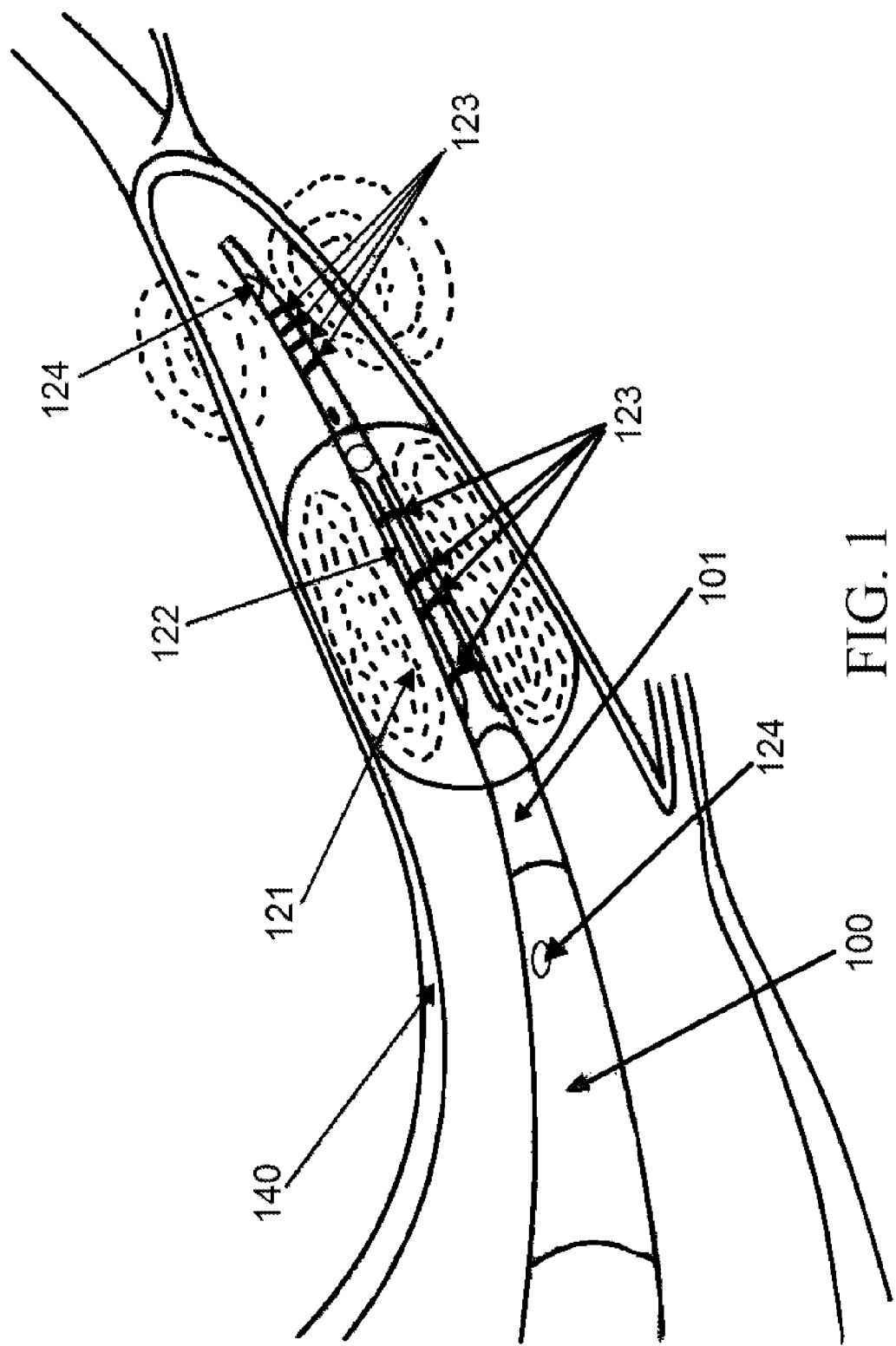
FIG. 1 shows a cannula within a vessel wall in which at a distal end, an external expandable balloon anchors the cannula in the coronary vein, while an internal balloon provides the necessary obstruction to cause a drop in pressure according to an exemplary embodiment of the present invention, wherein further impedance electrodes are placed distally to locally size the coronary sinus while additional electrodes are placed internal to the balloon for sufficient inflation and hence occlusion of the vein according to the distal size measurement.

An exemplary embodiment of the invention, illustrated in FIG. 1, shows a cannula 100 within a vessel wall 140, with the proximal portion (not shown) being a graft. The distal portion of the cannula includes a catheter 101 with an expandable external balloon 121. The catheter may be made of any appropriate material used in the art, such as polyurethane, silicone rubber, or other appropriate polymeric material. The distal end may also contain pressure sensors 124 for monitoring purposes and impedance electrodes 123 for measuring the vessel and sizing the external balloon 121 accordingly.

The external expandable balloon 121 anchors the cannula in the coronary vein. Additionally, the external balloon prevents backflow of blood leaving the cannula through the distal end. In this embodiment, a second, internal balloon 122 serves to provide the pressure drop required for gradual arterialization of the vein. The balloons may be made of any material suitable for their function, including but not limited to, polyethylene, latex, polyestherurethane, or combinations thereof. The balloons may be connected to secondary lumens within the cannula, which are, in one embodiment, connected to percutaneous ports emerging from the proximal end of the cannula. The percutaneous ports may be used to inflate or deflate the balloons during retroperfusion. In one exemplary embodiment, the internal balloon 122 may be removed completely via the secondary lumen when vein arterialization is complete. As in the embodiment illustrated in FIG. 1, an external balloon and an internal balloon may be concentric to each other. In other embodiments, the internal and external balloons may be located on distinct portions of the cannula.

Some exemplary embodiments may contain two tetrapolar sets of electrodes 123 to measure the vessel near the distal tip 120 of catheter and to size the balloon accordingly. The selective region of the coronary sinus can be sized using these excitation and detection electrodes as described in more detail within the pending patent application, "System and Method for Measuring Cross-Sectional Areas and Pressure Gradients in Luminal Organs," U.S. patent application Ser. No. 10/782,149, filed on Feb. 19, 2004, which is incorporated by reference herein in its entirety. In that application, a description is provided of a conductance catheter that is used to determine size of blood vessels.

In embodiments of the cannula that do not include impedance electrodes, the sizing of the exterior balloon may also be accomplished based on the compliance of the balloon measured ex vivo and in vivo. This method requires the calibration of the balloon volume and hence diameter in vitro subsequent to in vivo. This alternative method avoids the need for electrodes and impedance sizing but may be less accurate.

Once the lumen size of the applicable region of the coronary sinus is determined, the balloon is expanded accordingly. It is recalled that a vein is rather compliant at lower pressures and hence an appropriate diameter is selected to maintain the cannula lodged into the lumen. For acute applications, saline may be used to fill the balloon. For longer term applications, gels or silicones may be used to fill the balloon.

FIG. 2A shows the distal portion of the cannula 200 within the vessel wall 240. The body of the cannula houses two or more lumens with a variety of possible configurations, some of which are shown in FIG. 2B. In the embodiment illustrated, the cannula contains a primary lumen 203 and multiple secondary lumens 204. The secondary lumens may connect to an expandable exterior balloon 221 and/or interior balloon 222. The secondary lumen may also contain pressure sensors that allow internal monitoring of the cannula during retroperfusion.

The primary lumen 203 is the conduit that allows the oxygenated blood flow derived from an artery to flow into the coronary sinus. The lumen of the catheter is designed to provide an optimal stenosis geometry for the desired initial pressure drop and to ensure undisturbed flow in the coronary venous system. In various embodiments, the secondary lumens 204 may be used for a variety of different purposes, such as inflation, deflation, and removal of interior and exterior balloons, coronary sinus pressure measurement, cannula pressure measurement, and drug delivery. In one exemplary embodiment, the secondary lumens 204 are operatively coupled with proximal extensions that branch from the graft body in such way that they are employed as percutaneous access ports.

FIG. 3A presents a detailed illustration of an exemplary embodiment of a cannula, with its proximal end being a graft 302, that contains a stenosis which causes a drop in the pressure of blood passing through the cannula. The stenosis can be imposed by inflation of a balloon that partially occludes the lumen or by imposing a resorbable material within the lumen. A variety of materials may be used to construct the resorbable stenosis, such as, for example, polyols and magnesium alloy. The most widely used polyols are mannitol, sorbitol and maltitol. Mannitol is used in the description of the examples herein. A mold of the computed shape will be used to construct the stenosis using computer-assisted design while the magnesium alloy geometry will be sculpted by laser from a single tube. Mannitol is a naturally occurring nonreducing acyclic sugar compound widely used in foods, pharmaceuticals, medicine and chemical industries. Crystalline Mannitol exhibits a very low hygroscopicity, making it useful in products that are stable at high humidity.

Mannitol is often added in dried protein formulations as the bulking agent as it has the tendency to crystallize rapidly from aqueous solutions. It has recently been shown that acetylsalicylic acid, which is an active ingredient of aspirin, can be mixed with Mannitol without affecting its properties. This is ideal as it will provide antithrombotic properties to prevent coagulation of blood during the resorption of the stenosis. Alternatively, magnesium alloys may be used which are currently used in drug-eluting bioabsorbable stents. Magnesium is a natural body component with beneficial antithrombotic, antiarrythmic and antiproliferative properties. The degradation rate of magnesium alloy has been shown to be linear and complete after 2-3 months. The use of degradable magnesium alloys leads to electronegative and therefore, hypothrombogenic surfaces. As an essential element, slowly degrading magnesium should not harm tissue, particularly since magnesium solutions up to 0.5 mol/l are well tolerated if given parenterally. The mechanical properties and corrosion of magnesium alloys are quite controllable under physiological conditions and match the requirements for degradable stenosis. The stenosis mold 330 is then inserted into the catheter portion of the cannula very close to the proximal inlet. The graft 302 may then be glued at this junction as shown in FIG. 3A.

It should be noted that the resorption rate of mannitol is a function of molecular weight, crystallinity, and particle size. The compound is prepared so that it will resorb in approximately 8 weeks. The magnesium alloys have been shown to resorb within 8-12 weeks.

For balloon occlusions, the desired occlusion is obtained by measurement of pressure at the tip of the cannula during inflation of the balloon. Once the desired intermediate pressure is obtained, the balloon volume is finalized. The patient is allowed to arterialize at the pressure for some time. At the end of such period (typically 2-3 weeks), the occlusion is removed by deflation of the balloon. In an exemplary embodiment, the inner lumen containing the inner balloon may be removable and hence withdrawn.

The cannula is intended for insertion from either the axillary 341 or femoral (not shown) veins into the coronary sinus. The proximal graft 302 is anastomosed to the adjacent artery 342. The graft may be made of any biocompatible, nonresorbable polymer with the necessary strength to support the surrounding tissue and withstand pressure from blood flow and the necessary flexibility to form an anastomosis with between the artery and the vein within which the cannula is housed. For example, a material such as GORE-TEX (polytetraflouroethylene) is suitable for use in the graft. In exemplary embodiments, the total length of the graft is approximately 6 cm and that of the attached catheter is 8-10 cm, but they may be of any lengths such that their dimensions allow an anastomosis between the human coronary sinus and the subclavian artery to be made. Access ports 306 which connect to and are in fluid contact with the secondary lumens branch off of the proximal graft 302 in some embodiments.

The diameter within the cannula will, in certain exemplary embodiments, be approximately 4 mm, but may be of any diameter such that the cannula allows sufficient blood flow and can be accommodated by the relevant vessels. The geometry of the stenosis will be varied to ensure an approximately 50 mm Hg pressure drop and a sufficient entrance length into the coronary vein to ensure fully developed flow.

Figure 5B:
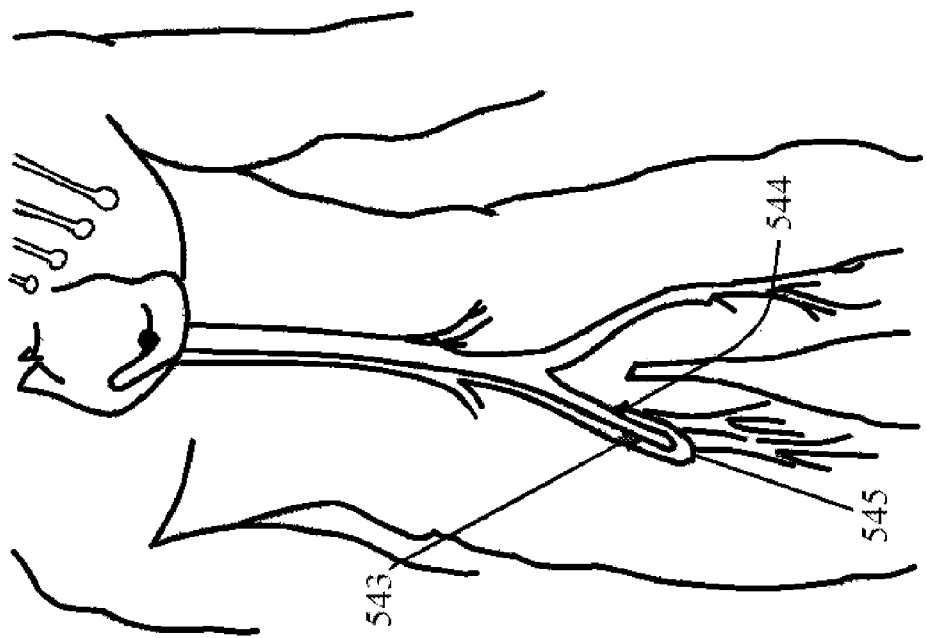
FIG. 5 shows the implantation of the auto-retroperfusion cannulae in the axillary and femoral regions.

To perform automatic retroperfusion using the present cannula, the axillary vein 441 and the axillary artery 442 are exposed as shown in FIGS. 4A-C and FIG. 5A. The same procedure may be performed using the femoral vein 543 and the femoral artery 544 as shown in FIG. 5B. The distal end portion of the cannula 400 is then introduced into the axillary vein 441. This may be done using the well-known Seldinger technique, which includes passing the cannula over a guide wire under fluoroscopy. The distal end portion of the cannula is then directed (via fluoroscopy, direct vision, transesophageal echocardiogram, or other suitable means) through the vasculature (e.g., the subclavian vein and the superior vena cava) and into the right atrium of the heart. The distal end portion of the cannula is further advanced through the right atrium and into the coronary sinus 446 as shown in FIG. 4B, which is the coronary vein. When the distal end portion of the cannula reaches the desired location in the coronary sinus, measurement of the sinus is made and the external balloon is inflated accordingly.

Next, an anastomosis 405 of the proximal graft portion 402 of the cannula and the artery 442 may be accomplished by suturing the graft section to the axillary artery as shown in FIG. 4C. This approach could be used for long term arterialization of the coronary venous system, which can replace coronary artery bypass graft.

Figure 5A:
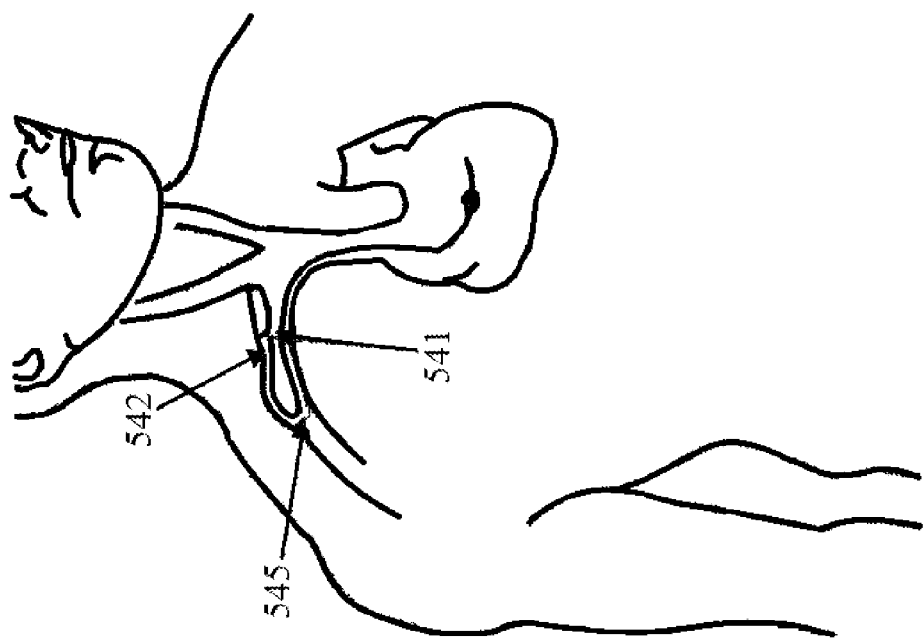

Alternatively, the autoretroperfusion cannula can be inserted by percutaneous puncture (under local anesthesia) in the axillary vein 541 and axillary artery 542 and both ends connected through a quick connector 545 (see FIG. 5A). This procedure may also be performed using the femoral vein 543 and artery 544, as shown in FIG. 5B. This procedure can be used for acute patients or for short periods of arterialization of the coronary veins to stabilize the patient as a bridge to another procedure.

Once the cannula is in place, normal antegrade blood flow continues as usual, but oxygenated blood will be automatically retroperfused through the cannula to the ischemic myocardium via the coronary sinus. The oxygenated blood flow through the cannula occurs throughout the cardiac cycle with a pulsatile flow pattern, but with a peak flow and pressure at the end of systole and the beginning of diastole. Back-flow of blood into the right atrium from the coronary sinus is prevented by the external expandable balloon of the cannula.

It should be noted that the aforementioned procedures can be done under local anesthesia. Depending on the patient's particular condition, auto-retroperfusion can last for minutes, hours, days, or months. During retroperfusion, the secondary lumens can be used for coronary sinus pressure measurement and the delivery of drugs, cells, genes, or growth factors. It is expected that the access ports 406 (see FIG. 4C), which are fluidly connected with the secondary lumens, and the graft section will be subcutaneous.

Figure 6A:
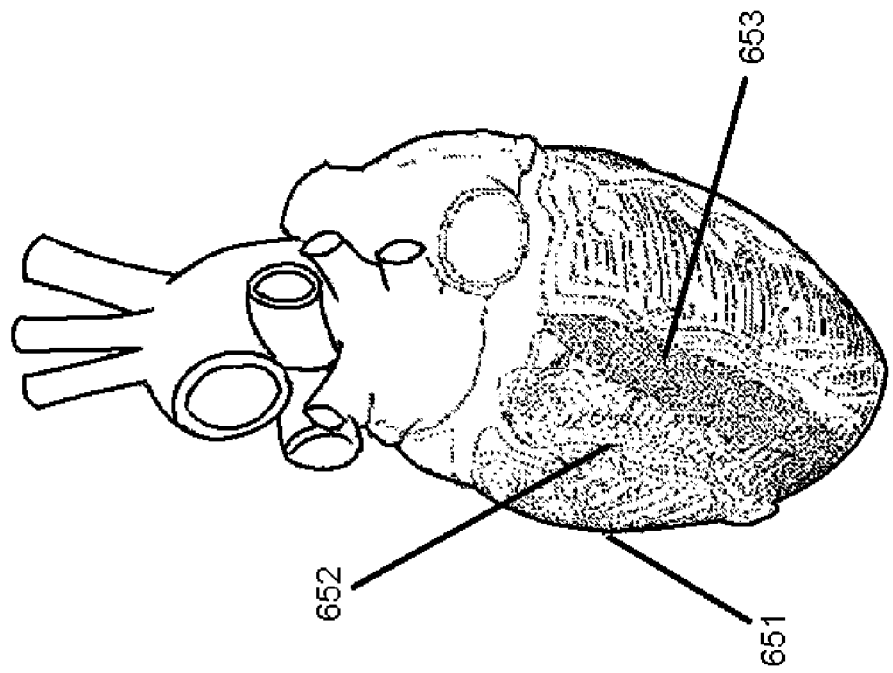
FIG. 6 shows a distribution of selective perfusion territories wherein Zone 1 corresponds to retroperfusion at the level of LAD interventricular anterior vein, which corresponds to the anterior and lateral wall of the left ventricle, and wherein Zone 2 is at the level of the obtuse marginal circumflex vein, and Zone 3 is at the level of the posterolateral circumflex vein.
Figure 6B:
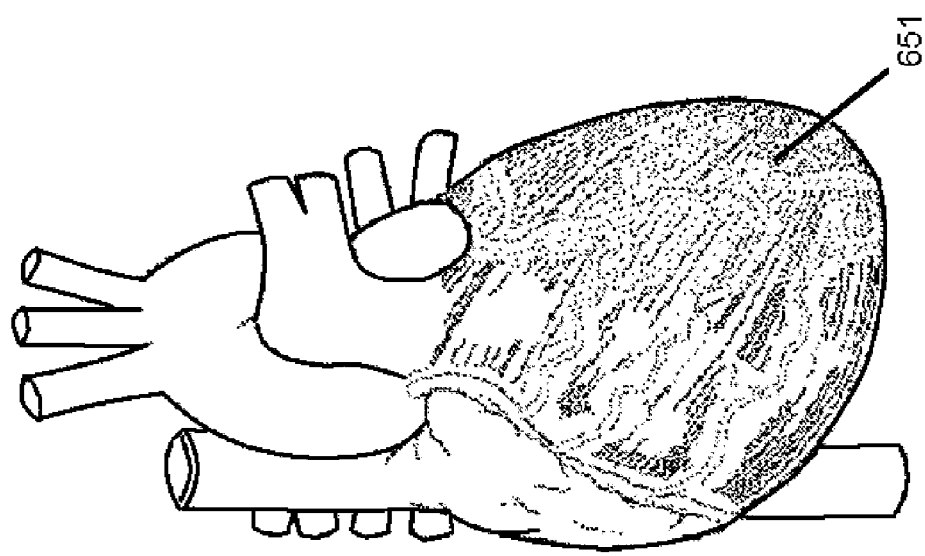

As this method is based on selective retroperfusion, there is a relationship between the site of the coronary sinus where the cannula is anchored and the region of the heart requiring treatment. FIGS. 6A-6B show several zones of interest. Zone 1 651, shown from an anterior view in FIG. 6A and from a posterior view in FIG. 6B, corresponds to retroperfusion at the level of the LAD interventricular anterior vein, which corresponds to the anterior and lateral wall of the left ventricle. This is the largest area of the left ventricle to be perfused and hence clinically the most relevant. This area is the most distal to the coronary sinus and can be determined by sizing of the vein through the impedance electrodes. Zone 2 652 covers the level of the obtuse marginal circumflex vein and is more proximal to the coronary sinus. Zone 3 653 covers the level of the posterolateral circumflex vein, which is the smallest area of the left ventricle to be perfused and is the most proximal to the coronary sinus. Hence, the position of the catheter, which can be determined by sizing of the vein through impedance measurements, can determine the perfusion territory. This will serve as a clinical strategy to treat patients with LAD or LCx disease.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device for controlling blood perfusion pressure within a vessel, the device comprising:
   an elongated body having a lumen, a proximal end configured for placement in a first area having a first blood pressure, a distal end configured for placement in a second area having a second blood pressure, and an anchoring balloon configured to anchor the elongated body within part of a circulatory system; and
   a resorbable stenosis positioned within the lumen of the elongated body between the proximal end and the distal end, the resorbable stenosis configured so not to fully occlude a blood vessel;
   wherein the resorbable stenosis is further configured to be resorbed over time when contacted by blood flowing from the proximal end to the distal end of the elongated body, thereby equalizing the first blood pressure at the first area with the second blood pressure at the second area.

2. The device of claim 1, wherein at least one of the proximal end and the distal end is/are configured for placement within a mammalian heart.

3. The device of claim 1, wherein the proximal end is configured for placement within an axillary artery or a femoral artery.

4. The device of claim 1, wherein the distal end is configured for placement within an axillary vein or a femoral vein.

5. The device of claim 1, wherein the resorbable stenosis comprises a material selected from the group consisting of polyols and magnesium alloy.

6. The device of claim 5, wherein at least one of the proximal end and the distal end is/are configured for placement within a mammalian heart.

7. The device of claim 5, wherein the proximal and is configured for placement within an axillary artery or a femoral artery.

8. The device of claim 5, wherein the distal end is configured for placement within an axillary vein or a femoral vein.

9. The device of claim 1, wherein the first blood pressure is higher than the second blood pressure.

10. The device of claim 1, wherein the equalizing of the first blood pressure at the first area with the second blood pressure at the second area is gradual.

11. The device of claim 1, wherein the device is a cannula.

12. A method for conditioning a blood vessel to operate under higher blood pressures, the method comprising:
    introducing a distal end of an elongated tubular body into a blood vessel to be conditioned, the blood vessel to be conditioned having a first blood pressure therein and the elongated tubular body comprising an interior having a stenosis and further comprising an anchoring balloon configured to anchor the elongated tubular body within part of a circulatory system, the stenosis configured so not to fully occlude the blood vessel to be conditioned;
    introducing a proximal end of the elongated tubular body into a second blood vessel such that blood flow is received within the interior of the elongated tubular body, the second blood vessel comprising a second blood pressure therein which is higher than the first blood pressure;
    inflating the anchoring balloon to anchor the elongated tubular body within the blood vessel or the second blood vessel; and reducing the size of the stenosis over time such that the first blood pressure at the distal end of the elongated body is approximately the same as the second blood pressure at the proximal end.

13. The method of claim 12, wherein the stenosis comprises a balloon occlusion and the step of reducing the size of the stenosis over time comprises deflating or removing the balloon occlusion positioned within the interior of the elongated tubular body.

14. The method of claim 12, wherein the stenosis comprises a resorbable stenosis and the step of reducing the size of the stenosis over time comprises the gradual resorption of the stenosis within the interior of the elongated tubular body.

15. The method of claim 14, wherein the gradual resorption of the stenosis within the interior of the elongated tubular body takes several weeks to complete.

16. The method of claim 14, wherein the stenosis comprises a material selected from the group consisting of polyols and magnesium alloy.

17. A cannula for creating retrograde flow within a part of a circulatory system, the cannula comprising:
an elongated body having a lumen, a proximal end configured for placement in a first area having a first blood pressure, a distal end configured for placement in a second area having a second blood pressure, and an anchoring balloon configured to anchor the elongated body within part of a circulatory system;
a resorbable stenosis positioned within the lumen of the elongated body between the proximal end and the distal end, the resorbable stenosis located closer to the proximal end than the distal end of the elongated body, the resorbable stenosis configured so not to fully occlude a blood vessel;
wherein the resorbable stenosis is configured to be resorbed over a period of time when contacted by blood flowing from the proximal end to the distal end of the elongated body such that the gradual equalization of the first blood pressure and the second blood pressure is achieved.

18. The device of claim 17, wherein at least one of the proximal end and the distal end is/are configured for placement within a mammalian heart.

19. The device of claim 17, wherein the proximal end is configured for placement within an axillary artery or a femoral artery.

20. The device of claim 17, wherein the distal end is configured for placement within an axillary vein or a femoral vein.

21. The device of claim 17, wherein the resorbable stenosis comprises a material selected from the group consisting of polyols and magnesium alloy.

22. The device of claim 21, wherein at least one of the proximal end and the distal end is/are configured for placement within a mammalian heart.

23. The device of claim 21, wherein the proximal end is configured for placement within an axillary artery or a femoral artery.

24. The device of claim 21, wherein the distal end is configured for placement within an axillary vein or a femoral vein.

* * * * *